United States Patent
Fremy et al.

(10) Patent No.: US 11,578,345 B2
(45) Date of Patent: Feb. 14, 2023

(54) FUNCTIONALISED POLYSULPHIDE SYNTHESIS METHOD

(71) Applicant: Arkema France, Colombes (FR)

(72) Inventors: Georges Fremy, Sauveterre de Bearn (FR); Arnaud Masselin, Saint Malo (FR)

(73) Assignee: Arkema France, Colombes (FR)

( * ) Notice: Subject to any disclaimer, the term of this patent is extended or adjusted under 35 U.S.C. 154(b) by 333 days.

(21) Appl. No.: 16/473,900

(22) PCT Filed: Dec. 21, 2017

(86) PCT No.: PCT/FR2017/053782
§ 371 (c)(1),
(2) Date: Jun. 26, 2019

(87) PCT Pub. No.: WO2018/122511
PCT Pub. Date: Jul. 5, 2018

(65) Prior Publication Data
US 2019/0338325 A1 Nov. 7, 2019

(30) Foreign Application Priority Data
Dec. 29, 2016 (FR) ..................... 16 63492

(51) Int. Cl.
*C12P 13/12* (2006.01)
*C07C 323/58* (2006.01)

(52) U.S. Cl.
CPC ............ *C12P 13/12* (2013.01); *C07C 323/58* (2013.01)

(58) Field of Classification Search
CPC .......... C12P 13/12; C12P 13/00; C12P 11/00; C07C 323/58
See application file for complete search history.

(56) References Cited

U.S. PATENT DOCUMENTS

| 3,022,351 | A | 2/1962 | Mihm et al. |
| 6,579,705 | B2 | 6/2003 | Maier et al. |
| 9,029,105 | B2 | 5/2015 | Kim et al. |
| 2011/0195945 | A1 | 8/2011 | Ruan et al. |

FOREIGN PATENT DOCUMENTS

| CN | 1379111 A | 11/2002 |
| CN | 103397057 A | 11/2013 |
| EP | 0844239 A1 | 5/1998 |
| WO | 2008013432 A1 | 1/2008 |
| WO | 2013029690 A1 | 3/2013 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Agren et al., Journal of Biological Chemistry 283(46):31567-31574.*
Branden et al., Introduction to Protein Structure, Garland Publishing Inc., New York, p. 247, 1991.*
Sadowski et al., Current Opinion in Structural Biology 19:357-362, 2009.*
Kreft et al., Plant Physiol. 104:1215-1220, 1994.*
Nagai, S., "Synthesis of O-acetylhomoserine", Academic Press, vol. 17, 1971—pp. 423-424.
Chocat et al., "Synthesis of Selenocystine and Selenohomocystine with O-Acetylhomoserine Sulfhydylase", Agric. Biol. Chem., 49(4), 1985—pp. 1143-1150.
Fletcher et al., "The Occurrence of Bis-(2-Amino-2-Carboxyethyl) Trisuiphide tn Hydrolysates of Wool and Other Proteins", Bochem. J., 87, 1963—pp. 553-559.
Guibé-Jampel et al., "Disulfide-bridge Formation through Solvent-free Oxidation of Thiol Amino Acids Catalysed by Peroxidase or Hemin on Mineral Supports", J. Chem. Soc. Perkin Trans. 1, 1999—pp. 3067-3068.
Kertmen et al., "Novel and Efficient Methods for the Synthesis of Symmetrical Trisulfides", Synthesis, No. 9, 2009—pp. 1459-1462.
Zhao et al., "Cloning, Overexpression, Purification, and Characterization of O-acetylserine Sulfhydrylase-B from *Escherichia coli*", Protein Expression and Purification, 47, 2006—pp. 607-613.
International Search Report and Written Opinion for International Application No. PCT/FR2017/053782, dated Apr. 23, 2018—10 pages.
PubChem 595—Cystine, Sep. 16, 2004, 1 page.
Chinese Office Action for Chinese Application No. 201780081528. 8, dated Jun. 10, 2022, with translation, 22 pages.

* cited by examiner

*Primary Examiner* — Delia M Ramirez
(74) *Attorney, Agent, or Firm* — RatnerPrestia

(57) ABSTRACT

Provided is process for the synthesis of at least one functionalized organic polysulfide.

4 Claims, No Drawings

FUNCTIONALISED POLYSULPHIDE SYNTHESIS METHOD

CROSS-REFERENCE TO RELATED APPLICATIONS

This is the national phase of International Application No. PCT/FR2017/053782, filed Dec. 21, 2017, which claims priority to French Application No. 1663492, filed Dec. 29, 2016. The disclosure of each of these applications is incorporated herein by reference in its entirety for all purposes.

FIELD OF THE INVENTION

The invention relates to the field of organic polysulfides and more particularly to a process for the synthesis of functionalized organic polysulfides.

BACKGROUND OF THE INVENTION

Organic polysulfides are used in numerous applications. This is because, depending on the functional groups which they carry, they can be used as additives in lubrication, as antiwear agent, extreme-pressure agent or antioxidant. They are also used during the presulfidation of catalysts for the hydrotreating of petroleum cuts or vulcanization. They can also participate in the composition of lubricating formulations, for example for gearboxes or for the machining of materials. Furthermore, they can be used in the manufacture of cement, concrete or asphalt. Finally, they can participate in the composition of some medicaments for combating radiation or for other therapeutic uses.

Consequently, depending on the organic polysulfides desired, there exist numerous processes for the synthesis of these compounds.

For example, in industry, organic polysulfides are commonly synthesized by a process of reaction between a mercaptan, sulfur and a basic catalyst. They can also be prepared by a process of reaction between an olefin of petroleum or renewable origin with sulfur and hydrogen sulfide. However, these processes for obtaining organic polysulfides require high temperature and/or pressure conditions in order to be effective.

It will be easily understood that, due to the multitude of the possible applications of functionalized organic polysulfides, there still exists a need to provide processes for the synthesis of the latter.

It will also be understood that there also exists a need for syntheses of functionalized organic polysulfides with processes which can be described as enduring, that is to say can be carried out with mild temperature and pressure conditions, in aqueous solution with pH values close to neutrality, and with starting materials of renewable origin, and the yields of which are greater than those obtained with the pre-existing processes, and more generally according to processes which are more environmentally friendly.

SUMMARY OF THE INVENTION

It has now been discovered that it is possible to meet the objectives defined above by carrying out the process according to the invention and as described below. Other objectives still will become apparent in the continuation of the description of the present invention which follows.

Thus, and according to a first aspect, the present invention relates to a process for the synthesis of at least one functionalized organic polysulfide of formula (I):

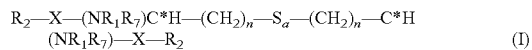
$$R_2-X-(NR_1R_7)C^*H-(CH_2)_n-S_a-(CH_2)_n-C^*H(NR_1R_7)-X-R_2 \qquad (I)$$

in which:
- $R_1$ and $R_7$, which are or are not different, are a hydrogen or an aromatic or nonaromatic, linear or cyclic, saturated or unsaturated, branched or unbranched, hydrocarbon chain of 1 to 20 carbon atoms, which can comprise heteroatoms;
- X is $-C(=O)-$ or $-CH_2-$ or $-CN$;
- $R_2$ is (i) either nonexistent (when X represents $-CN$), (ii) or a hydrogen, (iii) or $-OR_3$, $R_3$ being a hydrogen or an aromatic or nonaromatic, linear or cyclic, saturated or unsaturated, branched or unbranched, hydrocarbon chain of 1 to 20 carbon atoms, which can comprise heteroatoms, (iv) or $-NR_4R_5$, $R_4$ and $R_5$, which are or are not different, being a hydrogen or an aromatic or nonaromatic, linear or cyclic, saturated or unsaturated, branched or unbranched, hydrocarbon chain of 1 to 20 carbon atoms, which can comprise heteroatoms;
- n is equal to 1 or 2;
- a is an integer or decimal number between 2 and 10, preferably between 2 and 6; and
- * represents an asymmetric carbon;

said process comprising the stages of:
a/ providing at least one compound of formula (II):

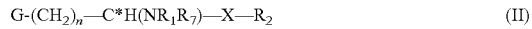
$$G-(CH_2)_n-C^*H(NR_1R_7)-X-R_2 \qquad (II)$$

in which:
- n, $R_1$, $R_2$, $R_7$, X and * are as defined above,
- G represents either (i) $R_6-C(=O)-O-$, or (ii) $(R_8O)(R_9O)-P(=O)-O-$, or (iii) $R_8O-SO_2-O-$;
- $R_6$ is a hydrogen or an aromatic or nonaromatic, linear or cyclic, saturated or unsaturated, branched or unbranched, hydrocarbon chain of 1 to 20 carbon atoms, which can comprise heteroatoms;
- $R_8$ and $R_9$, which are identical or different, being a proton H, an alkali metal, an alkaline earth metal or an ammonium, preferably a proton H or an alkali metal and more particularly a proton H or Na;

b/ providing at least one inorganic polysulfide;
c/ reaction between said at least compound of formula (II) and said at least inorganic polysulfide in the presence of at least one enzyme chosen from sulfhydrylases, and preferably a sulfhydrylase associated with said compound of formula (II);
d/ obtaining at least one functionalized organic polysulfide of formula (I);
e/ separation and isolation of said at least functionalized organic polysulfide of formula (I) and;
f/ optionally, additional functionalization of the functionalized organic polysulfide of formula (I) obtained in stage d/ or e/;

stages a/ and b/ being or not being carried out simultaneously.

DETAILED DESCRIPTION OF THE INVENTION

It has been observed that the configuration of the asymmetric carbon atoms is retained throughout the reaction. As other advantage, it should be noted that the functionalized organic polysulfide of formula (I) obtained according to the process according to the invention is an enantiomerically pure organic polysulfide.

"Functionalized organic polysulfide" is understood to mean any type of organic polysulfide of formula (I), the nitrogen atom of which carries a functional group (except when $R_1$ represents the hydrogen atom) and/or the carbon atom of which in the a position with respect to the nitrogen atom carries a functional group (except when —X— represents —CH$_2$— and when $R_2$ represents the hydrogen atom).

A better understanding of the invention will be obtained from the viewpoint of the description and of the examples which follow but the invention is not under any circumstances limited to said examples.

According to a preferred embodiment, $R_1$ and $R_7$ represent the hydrogen atom.

According to another preferred embodiment, X represents the —C(=O)— functional group.

According to another embodiment, $R_2$ represents —OR$_3$, $R_3$ being a hydrogen.

According to another embodiment of the invention, n is equal to 1.

According to yet another embodiment of the invention, n is equal to 2.

According to a preferred embodiment of the invention, within the formula (I), $R_1$ represents the hydrogen atom, X represents —C(=O)—, $R_2$ represents —OR$_3$ with $R_3$ being a hydrogen, n is equal to 1, and the compound of formula (I) is dicysteine polysulfide.

According to another preferred embodiment of the invention, within the formula (I), $R_1$ represents the hydrogen atom, X represents —C(=O)—, $R_2$ represents —OR$_3$ with $R_3$ being a hydrogen, n is equal to 2, and the compound of formula (I) is dihomocysteine polysulfide.

According to a preferred embodiment of the invention, within the formula (II), $R_1$ represents the hydrogen atom, X represents the C=O functional group, $R_2$ represents —OR$_3$ with $R_3$ being a hydrogen, n is equal to 1, and the compound of formula (II) is an L-serine derivative.

The L-serine derivative used in the process according to the invention can, for example and nonlimitingly, be chosen from O-phospho-L-serine, O-succinyl-L-serine, O-acetyl-L-serine, O-acetoacetyl-L-serine, O-propio-L-serine, O-coumaroyl-L-serine, O-malonyl-L-serine, O-hydroxymethylglutaryl-L-serine, O-pimelyl-L-serine and O-sulfo-L-serine.

Preferably, the L-serine derivative is chosen from O-phospho-L-serine, O-succinyl-L-serine, O-acetyl-L-serine and O-sulfo-L-serine.

Very particularly preferably, the L-serine derivative is O-acetyl-L-serine.

According to another preferred embodiment of the invention, within the formula (II), $R_1$ represents the hydrogen atom, X represents the C=O functional group, $R_2$ represents —OR$_3$ with $R_3$ being a hydrogen, n is equal to 2, and the compound of formula (II) is an L-homoserine derivative.

The L-homoserine derivative used in the process according to the invention can, for example and nonlimitingly, be chosen from O-phospho-L-homoserine, O-succinyl-L-homoserine, O-acetyl-L-homoserine, O-acetoacetyl-L-homoserine, O-propio-L-homoserine, O-coumaroyl-L-homoserine, O-malonyl-L-homoserine, O-hydroxymethylglutaryl-L-homoserine, O-pimelyl-L-homoserine and O-sulfo-L-homoserine.

Preferably, the L-homoserine derivative is chosen from O-succinyl-L-homoserine, O-acetyl-L-homoserine, O-phospho-homoserine and O-sulfo-L-homoserine.

Very particularly preferably, the L-homoserine derivative is O-acetyl-L-homoserine (OAHS).

The L-serine derivative and the L-homoserine derivative are either commercially available or obtained by any technique known to a person skilled in the art.

They can, for example, be obtained by fermentation of a renewable starting material. The renewable starting material can be chosen from glucose, sucrose, starch, molasses, glycerol or bioethanol, preferably glucose.

The L-serine derivative can also be produced from the acetylation of L-serine, it being possible for the L-serine itself to be obtained by fermentation of a renewable starting material. The renewable starting material can be chosen from glucose, sucrose, starch, molasses, glycerol or bioethanol, preferably glucose.

The L-homoserine derivative can also be produced from the acetylation of L-homoserine, it being possible for the L-homoserine itself to be obtained by fermentation of a renewable starting material. The renewable starting material can be chosen from glucose, sucrose, starch, molasses, glycerol or bioethanol, preferably glucose.

The inorganic polysulfide used in the process according to the invention has a mean whole or decimal sulfur rank of between 2 and 10, preferably between 2 and 6.

The inorganic polysulfide is chosen from alkali metal, alkaline earth metal and ammonium polysulfides.

Preferably, the inorganic polysulfide is chosen from sodium polysulfide, potassium polysulfide, calcium polysulfide and ammonium polysulfide.

Particularly preferably, the inorganic polysulfide is sodium polysulfide.

The inorganic polysulfide is prepared from hydrosulfide or sulfide according to any technique known to a person skilled in the art. The hydrosulfide or sulfide used can be an alkali metal, alkaline earth metal or ammonium hydrosulfide or sulfide.

The inorganic polysulfide can also be prepared from hydroxides, oxides, hydrogen sulfide or sulfur.

The amount of sulfur added is adjusted according to the mean sulfur rank desired for the inorganic polysulfide.

During the process according to the invention, the reaction between said at least compound of formula (II) and said at least inorganic polysulfide is carried out in the presence of at least one enzyme, said enzyme preferably being a sulfhydrylase associated with said compound of formula (II).

Thus, when the compound of formula (II) is an L-serine derivative, the enzyme which can be used is chosen from O-phospho-L-serine sulfhydrylase, O-succinyl-L-serine sulfhydrylase, O-acetyl-L-serine sulfhydrylase, O-acetoacetyl-L-serine sulfhydrylase, O-propio-L-serine sulfhydrylase, O-coumaroyl-L-serine sulfhydrylase, O-malonyl-L-serine sulfhydrylase, O-hydroxymethylglutaryl-L-serine sulfhydrylase, O-pimelyl-L-serine sulfhydrylase and O-sulfo-serine sulfhydrylase.

Preferably, the enzyme associated with the L-serine derivative is chosen from O-phospho-L-serine sulfhydrylase, O-succinyl-L-serine sulfhydrylase, O-acetyl-L-serine sulfhydrylase and O-sulfo-serine sulfhydrylase.

Very particularly preferably, the enzyme associated with the L-serine derivative is O-acetyl-L-serine sulfhydrylase.

When the compound of formula (II) is an L-homoserine derivative, the enzyme which can be used is chosen from O-phospho-L-homoserine, O-succinyl-L-homoserine sulfhydrylase, O-acetyl-L-homoserine sulfhydrylase, O-acetoacetyl-L-homoserine sulfhydrylase, O-propio-L-homoserine sulfhydrylase, O-coumaroyl-L-homoserine sulfhydrylase, O-malonyl-L-homoserine sulfhydrylase, O-hydroxymethylglutaryl-L-homoserine sulfhydrylase, O-pimelyl-L-homoserine sulfhydrylase and O-sulfo-L-homoserine sulfhydrylase.

Preferably, the enzyme associated with the L-homoserine derivative is chosen from O-phospho-L-homoserine sulfhydrylase, O-succinyl-L-homoserine sulfhydrylase, O-acetyl-L-homoserine sulfhydrylase and O-sulfo-L-homoserine sulfhydrylase.

Very particularly preferably, the enzyme associated with the L-homoserine derivative is O-acetyl-L-homoserine sulfhydrylase.

Said enzymes function, as fully known to a person skilled in the art, in the presence of a cofactor, such as pyridoxal 5'-phosphate.

The enzyme and its associated cofactor are generally dissolved in water before being added to the reaction medium. The amount of enzyme, with respect to the weight of the compound of formula (II), is between 0.1% and 10% by weight, preferably between 1% and 5% by weight, and the amount of cofactor, with respect to the compound of formula (II), is between 0.1% and 10% by weight, preferably between 0.5% and 5% by weight.

According to a preferred embodiment of the invention, the L-serine derivative is O-acetyl-L-serine, the inorganic polysulfide is sodium polysulfide and the enzyme used is O-acetyl-L-serine sulfhydrylase.

According to a preferred embodiment of the invention, the organic polysulfide obtained according to the process is dicysteine polysulfide.

According to another preferred embodiment of the invention, the L-homoserine derivative is O-acetyl-L-homoserine, the inorganic polysulfide is sodium polysulfide and the enzyme used is O-acetyl-L-homoserine sulfhydrylase.

According to a preferred embodiment of the invention, the organic polysulfide obtained according to the process is dihomocysteine polysulfide.

As regards the synthesis medium, temperature and pH conditions, reference may be made to those described in the applications WO2008013432 and WO2013029690.

Thus, according to the operating range of the enzyme, the reaction pH is between 5 and 8, preferably between 6 and 7.5 and more particularly between 6.2 and 7.2. In all cases, the pH has to be regulated according to the operating optimum of the enzyme. The pH can be regulated by addition of basic inorganic polysulfide, of dilute sulfuric acid or of dilute aqueous ammonia.

Thus, according to the operating range of the enzyme, the temperature during the reaction is between 10 and 45° C., preferably between 20 and 40° C. and more particularly between 25 and 37° C.

The reaction takes place in an aqueous medium or in the presence of organic solvents, if the latter are compatible with the enzymes used. Preferably, the reaction takes place in an aqueous medium.

The reaction can be carried out batchwise, semi-continuously or continuously. Reactors of any type which is known to a person skilled in the art may be suitable for reactions of this type.

According to one embodiment of the invention, the separation and the isolation of the organic polysulfide obtained can be carried out according to any technique known to a person skilled in the art, in particular by precipitation and filtration.

The optional stage f/ of the process according to the invention makes it possible to obtain additional functional groups which are different from those obtained after stage d/ or stage e/.

This is because the functionalized organic polysulfide of formula (I) obtained on conclusion of stage d/ can again be functionalized during this stage f/. For example, if $X-R_2$ represents a carboxyl functional group, the latter can be esterified, reduced to an aldehyde, reduced to an alcohol and then etherified, amidated, nitrilated or others. All the functional groups can be obtained by a person skilled in the art depending on the final use which is intended for the organic polysulfide.

Thus, the functionalized organic polysulfide of formula (I) obtained on conclusion of stage d/ can be subjected to one or more additional chemical reactions in order to obtain one or more organic polysulfides with different functional groups, said chemical reactions being all reactions known to a person skilled in the art.

The functionalized organic polysulfides of formula (I) obtained according to the process according to the invention can be used in numerous applications, such as lubrication, vulcanization, the sulfidation of catalysts, in the therapeutic field, and others.

In particular, the functionalized polysulfides of formula (I) can be used as antiwear agent, extreme-pressure agent or antioxidant. They can also participate in the composition of lubricating formulations or of some medicaments, such as medicaments for combating radiation. Finally, they can be used in the manufacture of cement, concrete or asphalt.

EXAMPLES

The examples which follow make it possible to illustrate the present invention but are not under any circumstances limiting.

Example 1: Synthesis of Dihomocysteine Tetrasulfide

Stage 1:

O-Acetyl-L-homoserine was synthesized from L-homoserine and acetic anhydride according to Sadamu Nagai, "Synthesis of O-acetyl-L-homoserine", Academic Press (1971), vol. 17, pp. 423-424.

Stage 2:

At the same time, 11.21 g of sodium hydrosulfide (200 mmol) are introduced into 100 ml of distilled water in a 250 ml glass reactor and are left to dissolve by stirring at ambient temperature using a thermostatically controlled oil bath. 9.62 g of flowers of sulfur (300 mmol) are gradually added over 2 h, the solution becomes red and $H_2S$ begins to degas from the reaction medium. This reactor is connected to a trap containing 200 g of 10% by weight sodium hydroxide solution (500 mmol of 100% NaOH). This sodium hydroxide solution makes it possible to trap the $H_2S$ originating from the reactor and also makes it possible to monitor the progression of the reaction by virtue of withdrawn samples analysed by argentometric potentiometric titration. A slight nitrogen flow is introduced into the reactor so as to facilitate the departure of the $H_2S$. After 2 hours, the analysis of the trap shows that 100% of the $H_2S$ theoretically produced has been trapped in the sodium hydroxide solution to form sodium hydrosulfide. Once this trap is saturated (sodium hydroxide completely converted) after several syntheses of sodium polysulfides, the sodium hydrosulfide solution can be used as is for the synthesis of these polysulfides. In the main reactor, 117.1 g of a $Na_2S_4$ solution titrating 14.9% by weight are obtained.

Stage 3:

10 g (62 mmol) of O-acetyl-L-homoserine (OAHS originating from stage 1) are introduced into 140 ml of distilled water in a thermostatically controlled 250 ml glass reactor. The solution is brought to 35° C. with mechanical stirring. The pH of the reaction medium is 4.8. It is desirable, before putting in the enzyme, for the pH to be equal to 6.5; for this, a few drops of the solution of sodium polysulfides obtained in stage 2 are added. A sample of 1 ml of the reaction medium is withdrawn (at t=0).

A solution of 10 ml of distilled water containing 400 µl of a solution of pyridoxal 5'-phosphate (10 mmol/l) and of 0.6 g of enzyme (O-acetyl-L-homoserine sulfhydrylase) is prepared and then this solution is added to the reactor. The reaction begins. The pH decreases and, in order to keep the reaction medium at a pH equal to 6.5, the sodium tetrasulfide solution is slowly added via the dropping funnel (in total, 36.2 g (i.e., 5.4 g de $Na_2S_4$ expressed as 100%-31 mmol) of the solution obtained during stage 2 are added). Samples (1 ml) are withdrawn during the reaction. The analyses by potentiometric titration, TLC, HPLC and UPLC/UV-mass show a gradual disappearance of the reactants (OAHS and $Na_2S_4$) and the gradual appearance, in increasingly large amounts, of the following compounds (it should be noted that a portion of these polysulfides precipitates during the reaction):

dihomocysteine disulfide (homocystine):

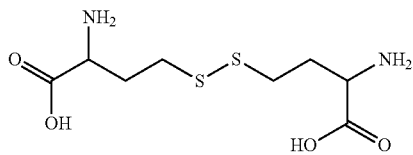

dihomocysteine trisulfide:

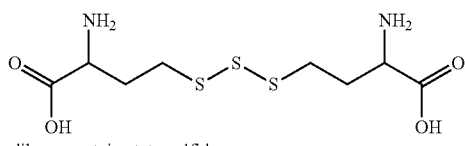

dihomocysteine tetrasulfide:

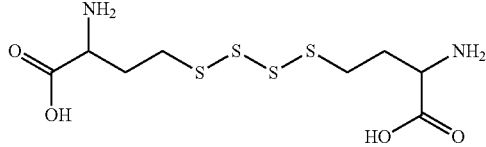

dihomocysteine pentasulfide:

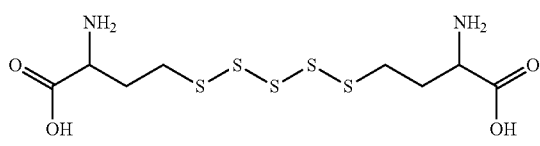

The only other products observed after the complete disappearance of the OAHS are traces of dihomocysteine (hydrolysis of the OAHS) and traces of homocysteine. It can thus be concluded therefrom that the synthesis of dihomoserine polysulfides (mean sulfur rank of 4) from OAHS has been virtually total.

Stage 4: Separation and Isolation of the Dihomocysteine Polysulfide:

The reaction medium of stage 3 is filtered a first time in order to recover, after drying, 4.4 g of dihomocysteine polysulfide. The residual solution is concentrated by partial evaporation of the water (so as to prevent the precipitation of the sodium acetate present in the reaction medium) under reduced pressure at 30° C.; a fresh precipitate is formed. After filtration and drying, 3.8 g of dihomocysteine polysulfide are again obtained. The overall isolated yield of homoserine polysulfide is 8.2 g with regard to theoretical 10.30 g, i.e. 79.6%.

Additional analyses on this dry product showed that this solid contained 41% (elemental analysis) of sulfur (thus a mean rank of 4.3) and that it did not contain elemental sulfur in the free state (HPLC analysis).

Example 2: Synthesis of Dihomocysteine Tetrasulfide (without Enzyme or Coenzyme)

Example 1 was repeated, with the only difference that the solution of pyridoxal 5'-phosphate and of enzyme (10 ml of distilled water containing 400 µl of a solution of pyridoxal 5'-phosphate (10 mmol/l) and of 0.6 g of enzyme (O-acetyl-L-homoserine sulfhydrylase)) was not added to the reactor. It turns out that the reaction does not start and that it is impossible to continually add the solution of sodium polysulfides while attempting to retain a pH of 6.5. On increasing to a pH equal to 8 by addition of sodium polysulfide solution, the only reaction observed is the beginning of hydrolysis of the OAHS to give homoserine. This example shows that this synthesis has to be catalyzed by an enzyme to be effective.

Example 3: Synthesis of Cysteine Disulfide (Cystine)

Stage 1:

O-Acetyl-L-serine is sold by Sigma-Aldrich. It can also be synthesized from L-serine by any means known to a person skilled in the art.

Stage 2:

11.21 g of sodium hydrosulfide (200 mmol) are introduced into 100 ml of distilled water in a 250 ml glass reactor and are left to dissolve by stirring at ambient temperature using a thermostatically controlled oil bath. 3.2 g of flowers of sulfur (100 mmol) are gradually added over 2 hours, the solution becomes bright yellow and $H_2S$ begins to degas from the reaction medium. This reactor is connected a trap containing 200 ml of 10% by weight sodium hydroxide solution (500 mmol of 100% NaOH). This sodium hydroxide solution makes it possible to trap the $H_2S$ originating from the reactor and to monitor the progression of the reaction by virtue of withdrawn samples analysed by argentometric potentiometric titration. A slight nitrogen flow is introduced into the reactor so as to facilitate the departure of the $H_2S$. After 2 hours, the analysis of the trap shows that 100% of the $H_2S$ theoretically produced has been trapped in the sodium hydroxide solution to form sodium hydrosulfide. Once this trap is saturated (sodium hydroxide completely converted) and after synthesis of sodium disulfide, the sodium hydrosulfide solution can be used as is for the synthesis of this disulfide. In the reactor, 111 g of a $Na_2S_4$ solution titrating 9.9% by weight are obtained.

Stage 3:

9.12 g (62 mmol) of O-acetyl-L-serine are introduced into 140 ml of distilled water in a thermostatically controlled 250 ml glass reactor. The solution is brought to 35° C. with mechanical stirring. The pH of the reaction medium is 4.6. It is desirable, before putting in the enzyme, for the pH to be 6.5; for this, a few drops of the solution of sodium disulfide ($Na_2S_2$) obtained in stage 2 are added. A sample of 1 ml of the reaction medium is withdrawn (at t=0). A solution of pyridoxal 5'-phosphate (10 mmol, 0.4 ml) and the enzyme O-acetyl-L-serine sulfhydrylase (0.6 ml) are dissolved in 10 ml of water and then added to the reactor. The reaction begins. The pH decreases and, in order to keep the reaction medium at a pH equal to 6.5, the sodium disulfide solution is slowly added via the dropping funnel (in total, 32 g of the solution obtained during stage 2, i.e. 3.2 g de $Na_2S_2$ expressed as 100%, 31 mmol, are added). Samples (1 ml) are withdrawn during the reaction. The analyses by potentiometric titration, TLC, HPLC and UPLC/UV-mass show a gradual disappearance of the reactants (O-acetyl-L-serine and $Na_2S_2$) and the gradual appearance of cystine. The appearance of a precipitate resulting from the formation of cystine is also observed:

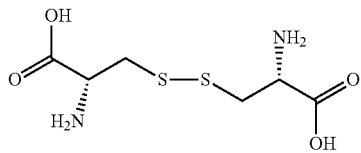 [SMILES: N[C@@H](CSSC[C@H](N)C(=O)O)C(=O)O]

The only other products observed after the complete disappearance of O-acetyl-L-serine are traces of serine (hydrolysis of O-acetyl-L-serine). It can thus be concluded therefrom that the synthesis of cystine from O-acetyl-L-serine has been virtually total.

Stage 4: Separation and Isolation of the Cystine:

The reaction medium of stage 3 is filtered a first time in order to recover, after drying, 4.7 g of cystine. The residual solution is concentrated by partial evaporation of the water (so as to prevent the precipitation of the sodium acetate present in the reaction medium) under reduced pressure at 30° C., and a fresh precipitate is formed. After filtration and drying, 1.2 g of cystine are again obtained. The overall isolated yield of cystine is 5.74 g with regard to theoretical 7.44 g, i.e. 77.2%. Additional analyses on this dry product showed that this solid contained 26.82% (elemental analysis) of sulfur (thus a mean rank of 2.01) and that it did not contain elemental sulfur in the free state (HPLC analysis).

The invention claimed is:

1. A process comprising the steps of:
(a) providing O-acetyl L-serine, O-phospho L-serine, or O-acetyl L-homoserine;
(b) providing at least one inorganic polysulfide;
(c) reacting the O-acetyl L-serine, O-phospho L-serine, or O-acetyl L-homoserine with the at least inorganic polysulfide in the presence of O-acetyl L-serine sulfhydrylase, O-phospho L-serine sulfhydrylase, or O-acetyl L-homoserine sulfhydrylase;
(d) obtaining at least one functionalized organic polysulfide of formula (I):

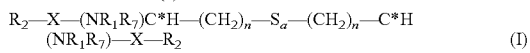
(I)

wherein:
$R_1$ is a hydrogen atom and $R_7$ is a hydrogen atom;
X is —C(=O)—;
$R_2$ is —$OR_3$, where $R_3$ is a hydrogen or a hydrocarbon containing 1 to 20 carbon atoms that can also contain heteroatoms, the hydrocarbon being aromatic or non-aromatic, linear or cyclic, saturated or unsaturated, branched or unbranched;
n is 1 or 2;
a is an integer between 2 and 10; and
C* represents an asymmetric carbon;
(e) separating and isolating the at least one functionalized organic polysulfide of formula (I); and
(f) optionally, adding functional groups different to those obtained in stage (d) or stage (e);
wherein stages (a) and (b) are carried out simultaneously or sequentially.

2. The process as claimed in claim 1, wherein the functionalized organic polysulfide of formula (I) is enantiomerically pure.

3. The process as claimed in claim 1, wherein the functionalized organic polysulfide of formula (I) is chosen from dicysteine polysulfide and dihomocysteine polysulfide.

4. The process as claimed in claim 1, wherein the inorganic polysulfide contains an alkali metal, an alkaline earth metal or an ammonium group.

* * * * *